(12) United States Patent
Masini

(10) Patent No.: US 6,306,173 B1
(45) Date of Patent: Oct. 23, 2001

(54) MODULAR ACETABULAR RECONSTRUCTION PLATE

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 0 days.

(21) Appl. No.: 09/432,560

(22) Filed: Nov. 3, 1999

Related U.S. Application Data

(63) Continuation of application No. 09/123,148, filed on Jul. 27, 1998, now Pat. No. 6,004,353.
(60) Provisional application No. 60/054,259, filed on Jul. 30, 1997.

(51) Int. Cl.$^7$ .................................................. A61F 2/34
(52) U.S. Cl. ..................................... 623/22.32; 623/22.38
(58) Field of Search ............................. 623/22.21, 22.32, 623/22.38

(56) References Cited

U.S. PATENT DOCUMENTS

| | | | |
|---|---|---|---|
| 4,573,458 | 3/1986 | Lower | 606/69 |
| 4,800,874 | 1/1989 | David et al. | 606/69 |
| 4,919,675 | 4/1990 | Dietschi | 623/22 |
| 4,959,072 | 9/1990 | Morscher et al. | 623/22 |
| 4,961,748 | 10/1990 | Frey | 623/22 |
| 4,966,599 | 10/1990 | Pollock | 606/69 |
| 5,030,238 | 7/1991 | Nieder et al. | 623/22 |
| 5,314,490 | 5/1994 | Wagner et al. | 623/22 |
| 5,326,367 | 7/1994 | Robioneck | 623/22 |
| 5,336,224 | 8/1994 | Selman | 606/69 |
| 5,372,598 | 12/1994 | Luhr | 606/69 |
| 5,425,778 | 6/1995 | Zichner et al. | 623/22 |
| 5,624,464 | 4/1997 | Wagner et al. | 623/22 |
| 5,702,477 | 12/1997 | Capello et al. | 623/22 |

FOREIGN PATENT DOCUMENTS

| | | | | |
|---|---|---|---|---|
| 4141977 | * | 7/1993 | (DE) | 623/22 |
| 0137664 | * | 4/1985 | (EP) | 623/22 |
| 2297030 | * | 8/1976 | (FR) | 623/22 |
| 2634372 | * | 1/1990 | (FR) | 623/22 |
| 2689000 | * | 10/1993 | (FR) | 623/22 |

* cited by examiner

*Primary Examiner*—David J. Isabella
(74) *Attorney, Agent, or Firm*—Gifford, Krass, Groh, Sprinkle, Anderson & Citkowski, PC

(57) ABSTRACT

Modular acetabular reconstruction apparatus includes a generally cup-shaped portion adapted for fixation within a human pelvis and one or malleable extension arms adjustable in multiple dimensions. Each arm preferably includes one or more apertured sections spaced apart from one another by a necked-down section enabling each arm to be manipulated in three dimensions for intimate physical conformity with surrounding bone. The back surface of the generally cup-shaped portion may be adapted for a cemented or a non-cemented interface within a human pelvis; as such, the back surface may be adapted for porous bone in-growth. According to a disclosed method, the step of bending each arm in multiple dimensions may be carried out a part of a trial joint reduction. Various bending tools and techniques are also set forth.

7 Claims, 3 Drawing Sheets

MODULAR ACETABULAR RECONSTRUCTION PLATE

REFERENCE TO RELATED APPLICATION

This application is a continuation of U.S. application Ser. No. 09/123,148, now U.S. Pat. No. 6,004,353, which claims priority of U.S. provisional application Ser. No. 60/054,259, filed Jul. 30, 1997, the entire contents of which are incorporated herein by reference.

FIELD OF THE INVENTION

This invention relates generally to orthopedics and, in particular, to a versatile reconstruction system associated with acetabular prosthetics.

BACKGROUND OF THE INVENTION

Especially in the case of revision surgical procedures wherein the pelvis has been severely compromised or deteriorated, it is known to use support structures to receive an acetabular prosthetic device.

One such structure is disclosed in U.S. Pat. No, 5,314,490 to Wagner et al, entitled OUTER CUP FOR AN ARTIFICIAL HIP JOINT SOCKET. According to this patent, an artificial hip joint socket for fastening to a pelvic bone includes a metallic outer cup forming a concavity for receiving a hip, which terminates in an equatorial edge to which supporting flaps are fastened. The flaps include holes to receive bone screws and have preset lines of grooves to enabling preferential bending to provide conformance with the pelvic region surrounding the procedure. The problem with this particular configuration, and others like it, is that, even with the grooves affording preferential bending, the flaps are not sufficiently malleable or adjustable in multiple dimensions to permit conformance to surrounding bone in all situations.

SUMMARY OF THE INVENTION

The present invention addresses a deficiency in the prior art by providing a more flexible, modular acetabular reconstruction plate and system of installation incorporating other advantages.

Apparatus according to the invention includes a generally cup-shaped portion having a peripheral rim and back surface adapted for fixation within a human pelvis, and one or more malleable extension arms connected to the rim of the cup-shaped portion. In the preferred embodiment, each malleable extension arm includes one or more apertured sections spaced apart from one another by a necked-down section, thus enabling each arm to be manipulated in three dimensions, as desired, so as to assume a shape in intimate conformity with surrounding bone.

To enhance installational stability, modular acetabular reconstruction apparatus according to the invention preferably includes at least one malleable extension arm adapted for overlying contact with the ilium of a human pelvis. One malleable extension arm adapted for overlying contact with the ischium of a human pelvis would also be advantageous. Laterally or medially oriented arms may further be provided, and in the event of pairs of arms which are sufficiently closely spaced, apart, malleable apertured bridge elements may further be provided between adjacent arms.

The back surface of the generally cup-shaped portion may be adapted for a cemented or a non-cemented interface within a human pelvis; as such, the back surface may be adapted for porous bone in-growth.

The invention further includes a method of treating a human acetabulum, wherein each malleable extension arm is manipulated in multiple dimensions, as required, so that each arm is in intimate physical conformity with the surrounding bone prior to fastening and fixation. Various bending tools and techniques are also disclosed in the accompanying detailed description and drawings which follow.

BRIEF DESCRIPTION OF THE DRAWINGS

FIG. 5A illustrates a first and second tools inserted into adjacent apertures to interact above the plane of the extension arm;

DETAILED DESCRIPTION OF THE INVENTION

Figure 1:
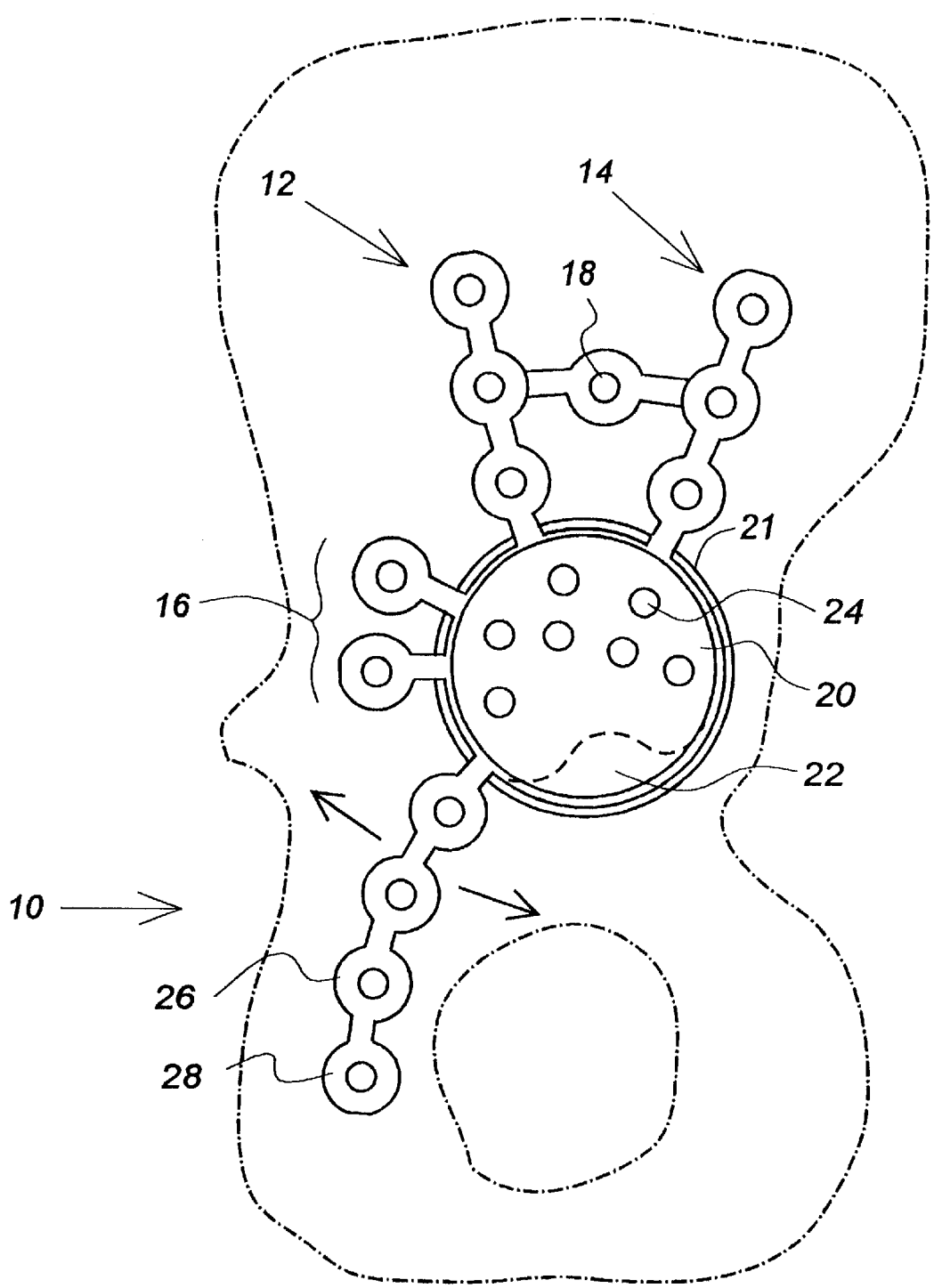
FIG. 1 is a lateral view of the acetabular area of a human pelvic region, depicted in conjunction with apparatus according to the invention featuring one or more outwardly extending arms with screw-receiving apertured sections between necked-down sections.

Now making reference to the accompanying drawings, FIG. 1 is a lateral view of the acetabular area of a pelvic region to which this invention applies. The apparatus includes a central plate portion 20 which is preferably in the form of a hemispherical socket or symmetrical cup. The plate 20 need not assume such a shape in all circumstances, however, as shown by broken line 22, which is used to indicate that, in situations where the bone itself is relieved relative to the acetabulum, the plate 20 may be relieved as well.

The plate 20 preferably includes a plurality of apertures 24 to receive bone screws and/or to provide a means for cement interdigitation. The plate further includes an outer edge 21 to which there is attached a plurality of malleable extension arms such as 10, 12 and 14. Although there may be more or fewer such arms than those depicted, their positioning is chosen to correspond to surrounding areas of "good bone" to better ensure stable anchoring.

A preferred embodiment includes two upwardly oriented malleable extension arms 12 and 14, and at least one lower arm 10, though others, such as 16, may be added as desired. An optional bridge element 18 between the members 12 and 14 may also be provided.

In contrast to prior-art devices, the arms 10, 12 and 14 preferably feature a series of sequential screw-receiving apertured sections such as 26 and 28, which are connected by necked-down sections such as 27, thereby enabling the apertured sections to be bent relative to one another in multiple dimensions.

Figure 2A:
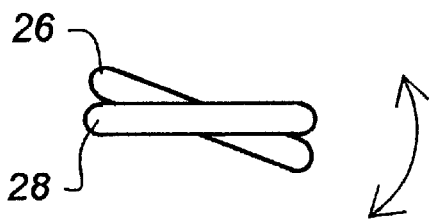
FIG. 2A shows how the outwardly extending arms of the invention may be tilted relative to one another to achieve improved conformity with surrounding bone.
Figure 2B:
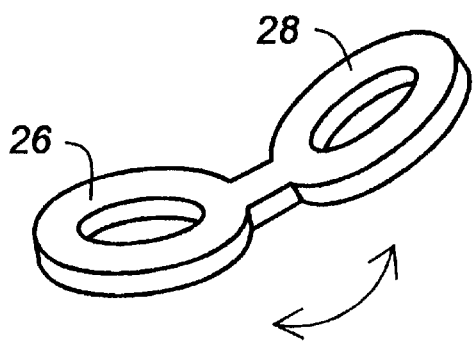
FIG. 2B shows how the outwardly extending arms of the invention may be angled to relative to one another.
Figure 2C:
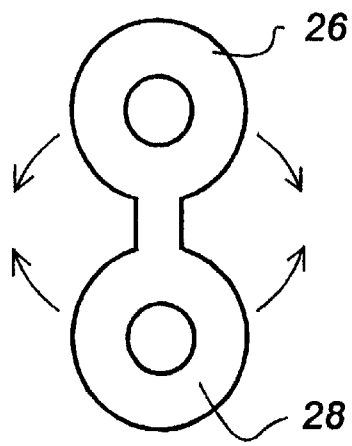
FIG. 2C shows how the outwardly extending arms of the invention may also be bent toward and away from one another.

For example, FIG. 2A shows how the sections 26 and 28 may be tilted relative to one another; FIG. 2B shows how the plates may be angled to relative to one another and, FIG. 2C illustrates with arrows how the plates 26 and 28 may also be bent toward and away from one another within the same plane.

Overall, owing to the shaped geometry of the extension arms, the apertured sections may be bent using one, more, or all of the degrees of freedom just described, thereby facilitating conformity to the surrounding bone in three dimensions. Another feature of preferred geometry is that one or more sections of an extension arm which are not required may easily be clipped off at an appropriate necked-down section.

According to a method of installing the inventive reconstruction system, a first step includes preparation of the acetabulum, as by reaming, to create a suitable bed such as a hemispherical cavity. Bone graft may be used to augment any deficient portions, using supplemental fixation as necessary. The central plate portion 20 is then placed into the prepared area, and contoured as necessary in accordance with surrounding bone, and then fixed it into place with bone screws, using either the holes in the plate 20 or those of the extension arms, depending optimum initial conformance. After stabilizing the device, the extension arms may then be bent as necessary to conform to the remaining bone and held into place at that point. Alternatively, one or more of the extension arms may be contoured prior to placement of the cup potion within the acetabulum.

Once installed, the central plate portion 20 is configured to receive a bearing surface, which may be constructed of polyethylene, ceramic or other material, as appropriate. According to another aspect of the invention, means may be provided for at least temporarily installing the bearing surface into the plate 20. In this way, the bearing surface may be temporarily removed for the introduction of cement.

In addition, the bending of the extension arms may be carried out partially or completely during a trial reduction. In this case, the bearing surface may be clipped into the plate 20, and, with the plate 20 including the bearing surface generally positioned into the acetabulum, a trial reduction may be performed. Assuming a successful trial, one or more screws may be used to hold the assembly in place, after which, having dislocated the joint, additional screws may be added, with the bearing surface being removed to gain access to the holes at the bottom portion of the plate 20, as required. It should be noted that the invention is applicable to both cemented and cementless configurations, such that, in accordance with the latter, a bone in-growth surface may be provided on at least the back side of the plate 20.

Figure 3A:
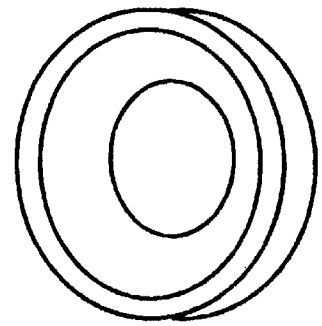
FIGS. 3A–3C illustrate alternative load-bearing insert configurations according to the invention.
Figure 3B:
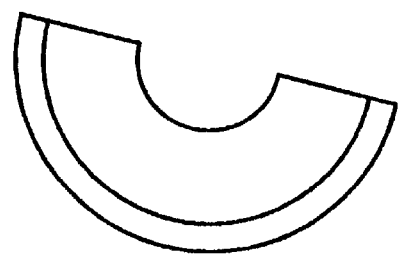
Figure 3C:
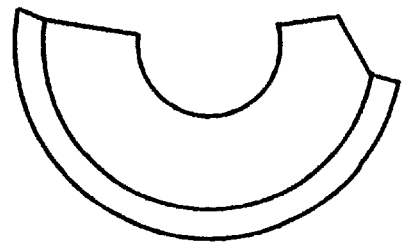

FIGS. 3A–3C illustrate alternative load-bearing insert configurations according to the invention. FIG. 3A illustrates an insert encompassing a full perimetry of the cup-shaped portion of the plate, whereas FIGS. 3B and 3C illustrate partial inserts having differently styled cut-out portions according to the extent of the required construction of other aspects of the surgical procedure. In the event that a slight repositioning of the bearing surface is to be made within the central plate, the bearing surface may be eccentrically formed along one or more dimensions, thereby enabling the insert to be installed and rocked or rotated until the correct positioning of the insert is established.

Figure 4:
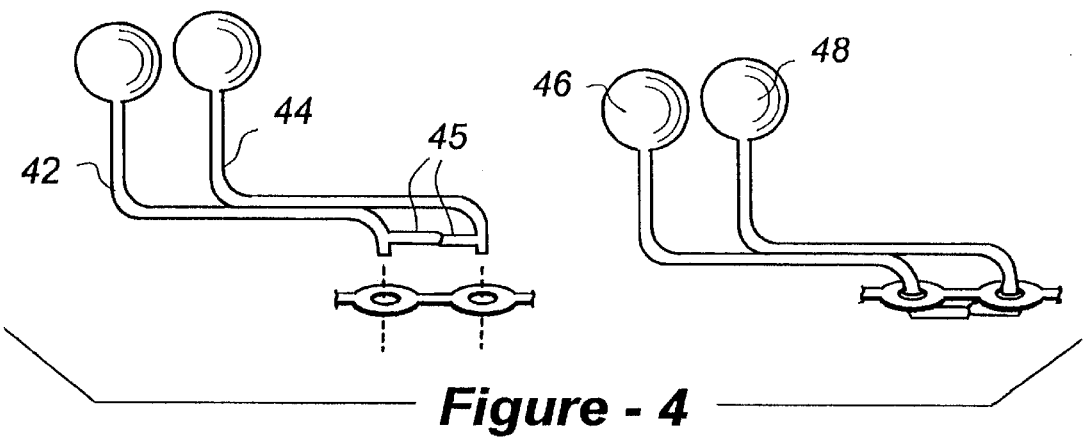
FIG. 4 is a diagram of tools according to the invention which may be used to more efficiently bend the extension arms.

FIG. 4 shows tools according to the invention which may be used to more efficiently bend the extension arms. Tools such as 42 and 44, for example, may be inserted into corresponding apertured sections and moved relative to one another to bend the extension arm. Protrusions 45 may be provided as points of leverage for more accurate manipulations. Tools such as 46 and 48 may be used in the event that insertion through a hole is desirable prior to bending.

FIG. 5 illustrates ways in which such benders would be applied. In FIG. 5A, a first tool 50 is inserted into one aperture and a second tool 52 is inserted into an adjacent aperture, with the protrusions between the two tools establishing a close interface 54 above the plane of the extension arm itself. These two facing protrusions may or may not touch, depending on the circumstances, having positioned the tools so as to create a desired bend.

Figure 5A:
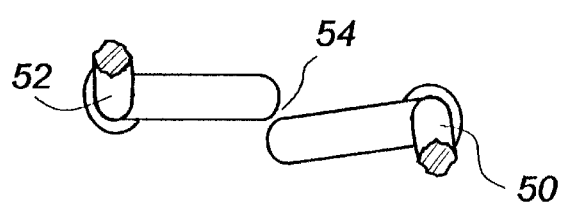
FIG. 5A begins a series of drawing which illustrate ways in which an inventive bending tool may be applied to adjust the extension arms. In particular.
Figure 5B:
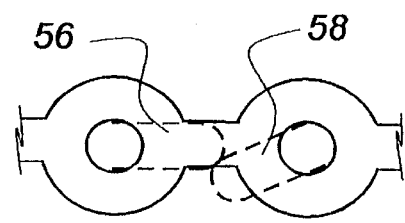
FIG. 5B illustrates how alternative first and second tools are inserted into adjacent aperture to interact below the plane of the extension arm.

The handle portions of the two tools 50 and 52 are then, for the most part, pressed toward one another causing the two holes to flip up relative to each other. FIG. 5B uses tools such as 46 and 48, which are inserted through adjacent holes such that the protrusions 56 and 58 are actually underneath the plane of the extension arms and, with the handles (not shown) pulled apart the apertured sections may be bent downwardly and away from one another.

Figure 5C:
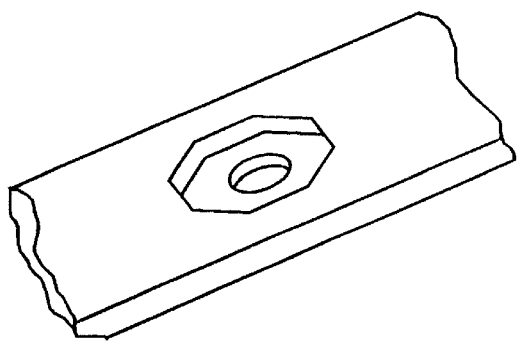
FIG. 5C shows how a portion of each screw-receiving hole may be non-round with a remaining portion of the hole being round or adapted for better conformance with the shaft or head of the particular fastener being used.
Figure 5D:
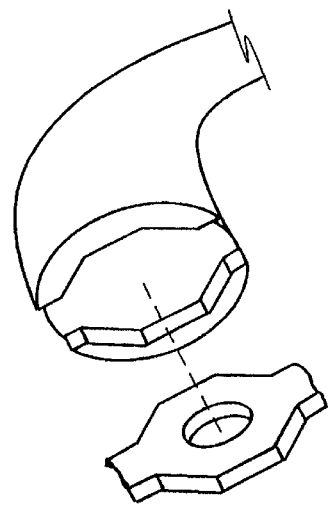
FIG. 5D depicts an alternative bending tool including inner surfaces which conform to the outer dimensions of the elements forming the extension plates.

As a further alternative, the aperture itself need not be round, but may be non-round, such as oval-shaped, hexagonal, octagonal, and so forth, enabling the end of the tool such as 48 shown in FIG. 4 to be similarly shaped, thereby preventing rotational movement during the bending process. As a further alternative, a portion of each hole may be non-round as disclosed above with a remaining portion of the hole being round or adapted for better conformance with the shaft or head of the screw being used, as shown in FIG. 5C. As shown in FIG. 5D, as an alternative to having a tool which conforms to the aperture, the tool may be made larger to include inner surfaces which conform to the outer dimensions of the elements forming the extension plates, as shown in FIG. 5D.

I claim:

1. Modular acetabular reconstruction apparatus, comprising:

a generally cup-shaped portion having a peripheral rim and a back surface, wherein at least a portion of the back surface includes porous bone in-growth material facilitating cementless fixation relative to a human pelvis;

one or more malleable extension arms connected to the peripheral rim of the cup-shaped portion facilitating fixation of the apparatus to surrounding bone;

two adjacent malleable extension arms adapted for overlying contact with the bone surrounding the acetabulum; and an apertured bridge element between the two arms.

2. The modular acetabular reconstruction apparatus of claim 1, wherein at least one of the extension arms includes one or more fastener-receiving apertures facilitating the fixation to surrounding bone.

3. The modular acetabular reconstruction apparatus of claim 1, further including a load-bearing insert to be received within the cup-shaped portion.

4. The modular acetabular reconstruction apparatus of claim 3, wherein the load-bearing insert features a rim which is exposed when the insert is installed relative to the rim of the apparatus.

5. The modular acetabular reconstruction apparatus of claim 3, wherein the load-bearing portion of the insert is eccentric with respect to the cup-shaped position.

6. The modular acetabular reconstruction apparatus of claim 3, wherein the load-bearing insert is cementable within the cup-shaped portion.

7. The modular acetabular reconstruction apparatus of claim 1, wherein the malleable extension arm further includes one or more necked-down sections enabling the arm to be manipulated in three dimensions for intimate conformity with surrounding bone.

* * * * *